US010888680B2

(12) United States Patent
Zickefoose et al.

(10) Patent No.: US 10,888,680 B2
(45) Date of Patent: Jan. 12, 2021

(54) ENDOTRACHEAL TUBE HOLDER DEVICE

(71) Applicant: TELEFLEX MEDICAL INCORPORATED, Morrisville, NC (US)

(72) Inventors: Aaron K. Zickefoose, Fuquay-Varina, NC (US); Jorge J. Perez, Raleigh, NC (US); Douglas R. Drew, Raleigh, NC (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 533 days.

(21) Appl. No.: 15/074,359

(22) Filed: Mar. 18, 2016

(65) Prior Publication Data

US 2016/0271349 A1  Sep. 22, 2016

Related U.S. Application Data

(60) Provisional application No. 62/134,846, filed on Mar. 18, 2015.

(51) Int. Cl.
*A61M 16/04* (2006.01)

(52) U.S. Cl.
CPC ..... *A61M 16/0497* (2013.01); *A61M 16/0434* (2013.01)

(58) Field of Classification Search
CPC .......... A61M 16/0497; A61M 16/0434; A61M 16/0488; A61M 16/0493; A61M 25/02; A61M 2025/026; A61M 2025/0266; A61M 2025/0206
See application file for complete search history.

(56) References Cited

U.S. PATENT DOCUMENTS

| 3,713,448 A | 1/1973 | Arrott |
| 3,756,244 A | 9/1973 | Kinnear et al. |
| 3,924,636 A | 12/1975 | Addison |

(Continued)

FOREIGN PATENT DOCUMENTS

| JP | H07-331714 | 12/1995 |
| KR | 100909101 | 8/2008 |

(Continued)

OTHER PUBLICATIONS

International Search Report and Written Opinion issued in PCT/US19/22466, dated Jun. 6, 2019.

*Primary Examiner* — Ophelia A Hawthorne
(74) *Attorney, Agent, or Firm* — BakerHostetler

(57) ABSTRACT

The present disclosure relates to a device for holding an endotracheal tube. The device includes a rail having opposite ends and a plurality of grooves at least partially along the length of the rail between the opposite ends. The device also includes a tube holder coupled to and slidable relative to the rail between the opposite ends. The tube holder includes at least one lever arm partially received with the grooves of the rail to allow lateral repositioning of the tube holder relative to the rail, a tie having a slit and a plurality of teeth, a base extending away from a patient relative to the at least one lever arm, and a tab extending laterally from the tube holder with the tab configured to be received within the slit of the tie. The base includes a pawl configured to engage at least one of teeth of the tie.

23 Claims, 9 Drawing Sheets

(56) References Cited

U.S. PATENT DOCUMENTS

| | | | |
|---|---|---|---|
| 3,946,742 A | 3/1976 | Eross | |
| 4,270,529 A | 6/1981 | Muto | |
| 4,326,515 A | 4/1982 | Shaffer et al. | |
| 4,351,331 A | 9/1982 | Gereg | |
| 4,449,527 A | 5/1984 | Hinton | |
| 4,683,882 A | 8/1987 | Laird | |
| 4,744,358 A | 5/1988 | McGinnis | |
| 4,774,944 A | 10/1988 | Mischinski | |
| 4,832,019 A | 5/1989 | Weinstein et al. | |
| 4,867,154 A | 9/1989 | Potter et al. | |
| 4,906,234 A | 3/1990 | Voychehovski | |
| 5,009,227 A | 4/1991 | Nieuwstad | |
| 5,341,802 A | 8/1994 | Calebaugh | |
| 5,345,931 A | 9/1994 | Battaglia, Jr. | |
| 5,419,319 A | 5/1995 | Werner | |
| 5,437,273 A | 8/1995 | Bates et al. | |
| 5,490,504 A | 2/1996 | Vrona et al. | |
| 5,513,633 A | 5/1996 | Islava | |
| 5,551,421 A | 9/1996 | Noureldin et al. | |
| 5,555,881 A | 9/1996 | Rogers et al. | |
| 5,649,534 A | 7/1997 | Briggs, III | |
| 5,829,430 A | 11/1998 | Islava | |
| 6,010,484 A | 1/2000 | McCormick et al. | |
| 6,050,263 A | 4/2000 | Choksi et al. | |
| 6,067,985 A | 5/2000 | Islava | |
| 6,105,577 A | 8/2000 | Varner | |
| 6,561,192 B2 | 5/2003 | Palmer | |
| 6,578,576 B1 | 6/2003 | Taormina et al. | |
| 6,634,359 B1 | 10/2003 | Rudy, Jr. et al. | |
| 6,810,878 B2 | 11/2004 | Palmer | |
| 7,017,579 B2 | 3/2006 | Palmer | |
| 7,063,088 B1 * | 6/2006 | Christopher | A61M 16/0488 128/207.14 |
| 7,231,921 B2 | 6/2007 | Palmer | |
| 7,896,004 B2 | 3/2011 | Yang | |
| 8,096,300 B2 | 1/2012 | Russo | |
| 8,156,934 B2 | 4/2012 | Trodler | |
| 8,256,427 B2 | 9/2012 | Chang et al. | |
| 8,302,597 B2 | 11/2012 | Beely et al. | |
| 8,636,008 B2 | 1/2014 | Flory et al. | |
| 8,726,903 B2 | 5/2014 | Levine | |
| 9,233,221 B2 | 1/2016 | Haider et al. | |
| 9,308,340 B2 | 4/2016 | Bond et al. | |
| 9,381,315 B2 | 7/2016 | Chin | |
| 9,707,364 B2 | 7/2017 | Islava | |
| D804,659 S | 12/2017 | Hood | |
| 9,981,101 B2 | 5/2018 | VanMiddendorp et al. | |
| 2005/0133038 A1 | 6/2005 | Rutter | |
| 2010/0083970 A1 | 4/2010 | Beely et al. | |
| 2011/0240034 A1 * | 10/2011 | Ciccone | A61M 16/0493 128/207.17 |
| 2013/0068233 A1 | 3/2013 | De Lulio et al. | |
| 2014/0238406 A1 | 8/2014 | Borre et al. | |
| 2014/0261462 A1 | 9/2014 | Visconti et al. | |
| 2014/0261463 A1 | 9/2014 | Visconti et al. | |
| 2016/0121067 A1 | 5/2016 | VanMiddendorp et al. | |
| 2016/0235935 A1 | 8/2016 | Mirza et al. | |
| 2016/0271349 A1 | 9/2016 | Zickefoose et al. | |
| 2016/0279367 A1 | 9/2016 | Kanowitz | |
| 2016/0361509 A1 | 12/2016 | Blessing, Jr. et al. | |
| 2017/0173288 A1 | 6/2017 | Stam et al. | |
| 2017/0197049 A1 | 7/2017 | Doll | |
| 2018/0099112 A1 | 4/2018 | Belenkiy | |
| 2018/0207381 A1 | 7/2018 | Winthrop et al. | |

FOREIGN PATENT DOCUMENTS

| | | |
|---|---|---|
| WO | 2015127443 A1 | 8/2015 |
| WO | 2016114643 A1 | 7/2016 |
| WO | 2016116916 A1 | 7/2016 |
| WO | 2017145101 A1 | 8/2017 |
| WO | 2017179780 A1 | 10/2017 |
| WO | 2018071804 A2 | 4/2018 |

* cited by examiner

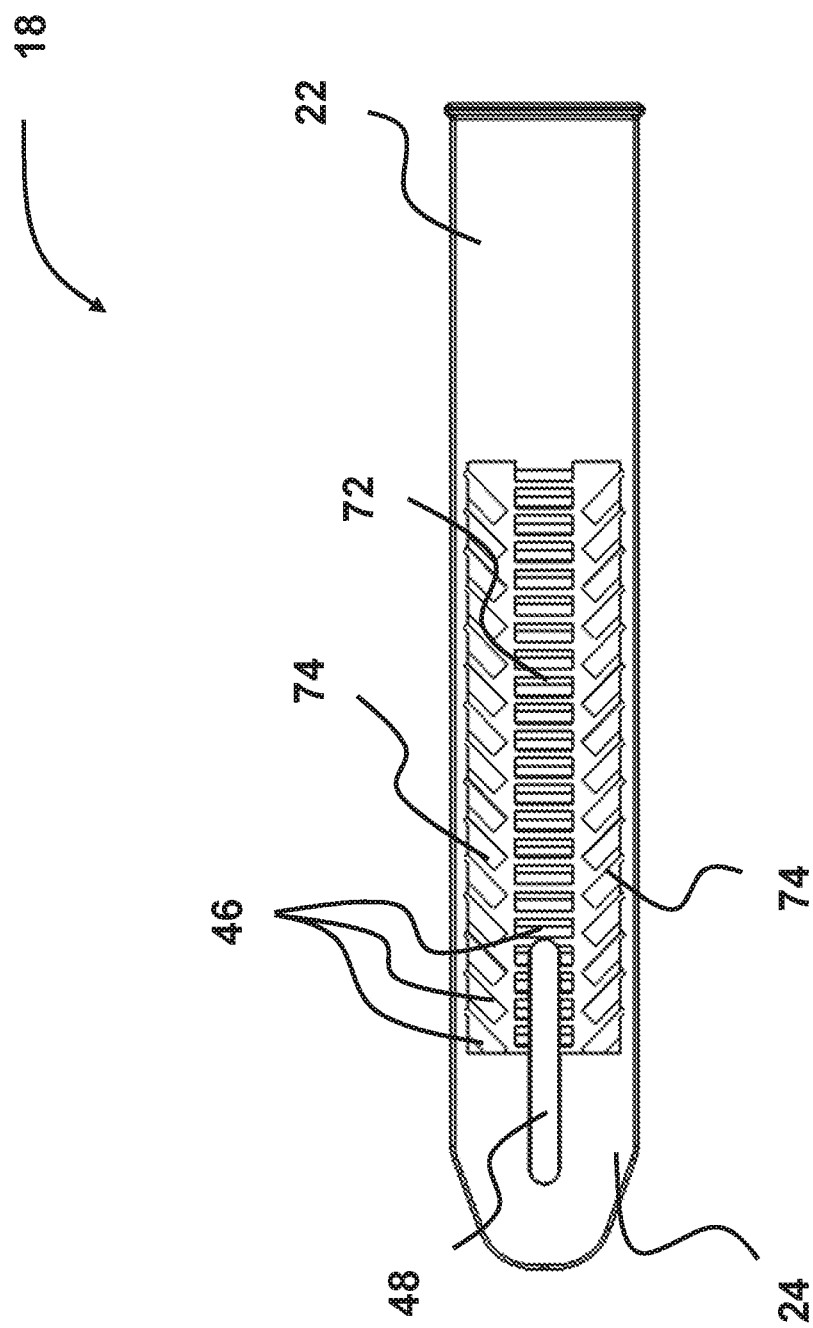

ENDOTRACHEAL TUBE HOLDER DEVICE

CROSS-REFERENCE TO RELATED APPLICATION

This application claims priority to U.S. provisional patent application No. 62/134,846, filed Mar. 18, 2015, the disclosure of which is hereby incorporated by reference in its entirety.

FIELD OF THE INVENTION

The disclosure generally relates to medical tube holders, and more particularly to a device for holding an endotracheal tube.

BACKGROUND

Endotracheal tubes are inserted into the trachea of a patient to establish and maintain a patient's airway during resuscitation, anesthesia, and other critical care procedures. Endotracheal tubes help deliver air to patients who cannot breathe on their own due. They are often placed prior to surgery or are used for critically ill patients that require assistance breathing for extended periods of time. Once inserted, endotracheal tubes must be fastened in a fixed position to prevent movement of the endotracheal tube for periods of up to several days.

In order to properly secure the endotracheal tube to an endotracheal tube holder, known designs have disclosed a variety of securement methods. However, in many of these methods, it difficult and time-consuming to release the endotracheal tube before or after intubation, which causes discomfort for the patient. Accordingly, there is a need for an endotracheal tube holder device with an improved tube holder mechanism.

SUMMARY OF THE INVENTION

The foregoing needs are met, to a great extent, by the endotracheal tube holder device disclosure below. In one or more aspects, the device for holding an endotracheal tube includes a rail having opposite ends and a plurality of grooves at least partially along the length of the rail between the opposite ends. The device also includes a tube holder coupled to and slidable relative to the rail between the opposite ends. The tube holder includes at least one lever arm partially received with the grooves of the rail to allow lateral repositioning of the tube holder relative to the rail, a tie having a slit and a plurality of teeth, a base extending away from a patient relative to the at least one lever arm, and a tab extending laterally from the tube holder with the tab configured to be received within the slit of the tie. The base includes a pawl configured to engage at least one of teeth of the tie.

In some aspects, the pawl can include a lever configured to release the tie when the lever is depressed. The base can define a slot configured to receive one end of the tie at a first lateral portion of the base. The pawl can be configured to receive the opposing end of the tie at a second lateral portion of the base opposite the first lateral portion. The tab can extend laterally from the first lateral portion of the tube holder. The tab can include a knob having a diameter greater than the width of the slit.

In further aspects, an adhesive tape can be applied to an inner surface of the tie that contacts an outer surface of the endotracheal tube. The adhesive tape can be applied to a first end region of the tie. The slit can be located on a second end region of the tie opposing the first end region. The slit can extend at least partially along an axial length of the tie. The slit can extend at least partially across the plurality of teeth.

In yet further aspects, a bottom of the base can include a plurality of barbs to engage the endotracheal tube. The tube holder can also include a bite block configured to extend into the mouth of the patient. The bite block can have a substantially cylindrical shape defining an axial opening along an entirety of the length of the bite block. A hydrocolloid pad can be coupled to each of the opposite ends of the rail.

In still further aspects, the at least one lever arm can be configured to be laterally compressed to laterally reposition the tube holder relative to the rail. The plurality of teeth can be formed on an inner surface of the tie that contacts an outer surface of the endotracheal tube. The plurality of teeth can have a pattern selected from the group consisting of a sawtooth wave, a square wave, a rectangular wave, a trapezoidal wave, a triangular wave, and a combination thereof. The plurality of teeth can also include a first section along a width of the tie having a first pattern and a second section along the width of the tie outside of the first section having a second pattern, the second pattern being different from the first pattern. The rail can be configured to be placed above a lip of the patient.

In some aspects a kit can include an endotracheal tube and the device for holding the endotracheal tube.

Certain aspects of the endotracheal tube holder device have been outlined such that the detailed description thereof herein may be better understood and in order for the present contribution to the art may be better appreciated. There are, of course, additional aspects of the disclosure that will be described below and which will form the subject matter of the claims appended hereto.

In this respect, before explaining at least one aspect of the endotracheal tube holder device in detail, it is to be understood that the endotracheal tube holder device is not limited in its application to the details of construction and to the arrangements of the components set forth in the following description or illustrated in the drawings. The endotracheal tube holder device is capable of aspects in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods, and systems for carrying out the several purposes of the endotracheal tube holder device. It is important, therefore, that the claims be regarded as including such equivalent constructions insofar as they do not depart from the spirit and scope of the disclosure.

BRIEF DESCRIPTION OF THE DRAWINGS

In order that the disclosure may be readily understood, aspects of the endotracheal tube holder device are illustrated by way of examples in the accompanying drawings.

FIG. 8 is a top view of a tie of another aspect of the endotracheal tube holder device.

DETAILED DESCRIPTION

Figure 1:
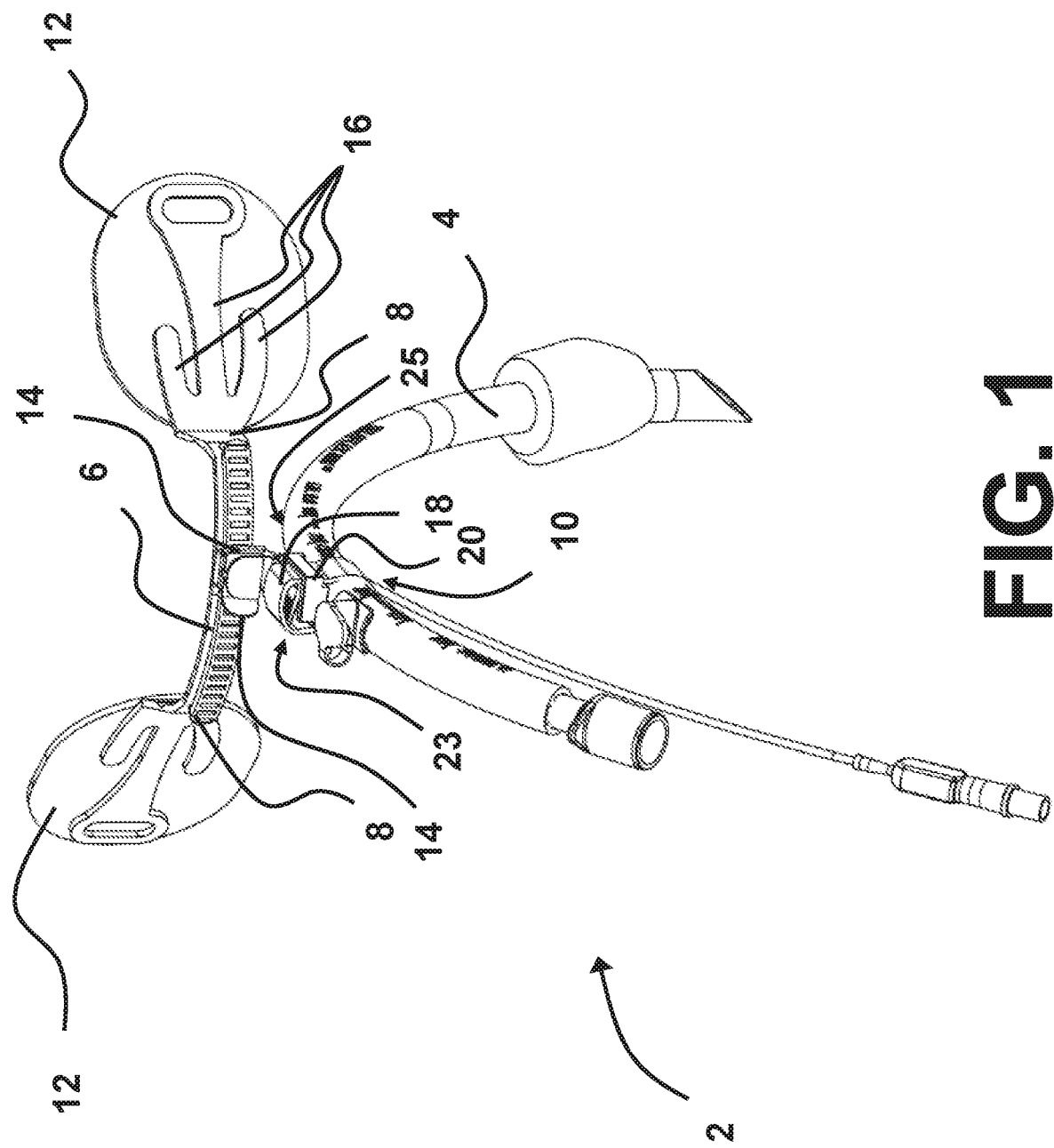
FIG. 1 is a perspective view of an endotracheal tube holder device holding an endotracheal tube.

FIG. 1 illustrates an endotracheal tube holder device 2 for securing an endotracheal tube 4. The device has a rail 6 configured to fit across a patient's face above the patient's lip. Specifically, the rail 6 has a curved design to lie horizontally across the patient's face. The rail 6 also has two opposite ends 8. At each opposite end 8, the rail 6 is attached to a pad 12 designed to contact the patient's cheeks. The endotracheal tube holder device 2 also includes a tube holder 10 that is coupled to and slidable along the rail 6 between the opposite ends 8. The tube holder 10 has a pair of lever arms 14 designed to allow selective lateral repositioning of the tube holder 10 relative to the rail 6. The rail 6 and the tube holder 10 may be made from a durable, rigid plastic material such as polypropylene or polyethylene. It may be desirable that rail 6 is made from a plastic material that is somewhat flexible to better curve around a patient's face.

The pads 12 may be made of a hydrocolloid dressing or some other skin friendly dressing. The pads 12 may have an adhesive (not shown) applied to the skin contacting surface to improve adherence of the pads 12 to the patient. Although the pads depicted in FIG. 1 are flat, the pads 12 may also be contoured to match the shape of a patient's face. The pads 12 are coupled to the rail 6 along a plurality of rail fingers 16. As shown in FIG. 1, there are three rail fingers 16 at each end 8 of the rail 6. In other aspects, however, a different number of rail fingers 16 can be at each end 8.

Figure 2:
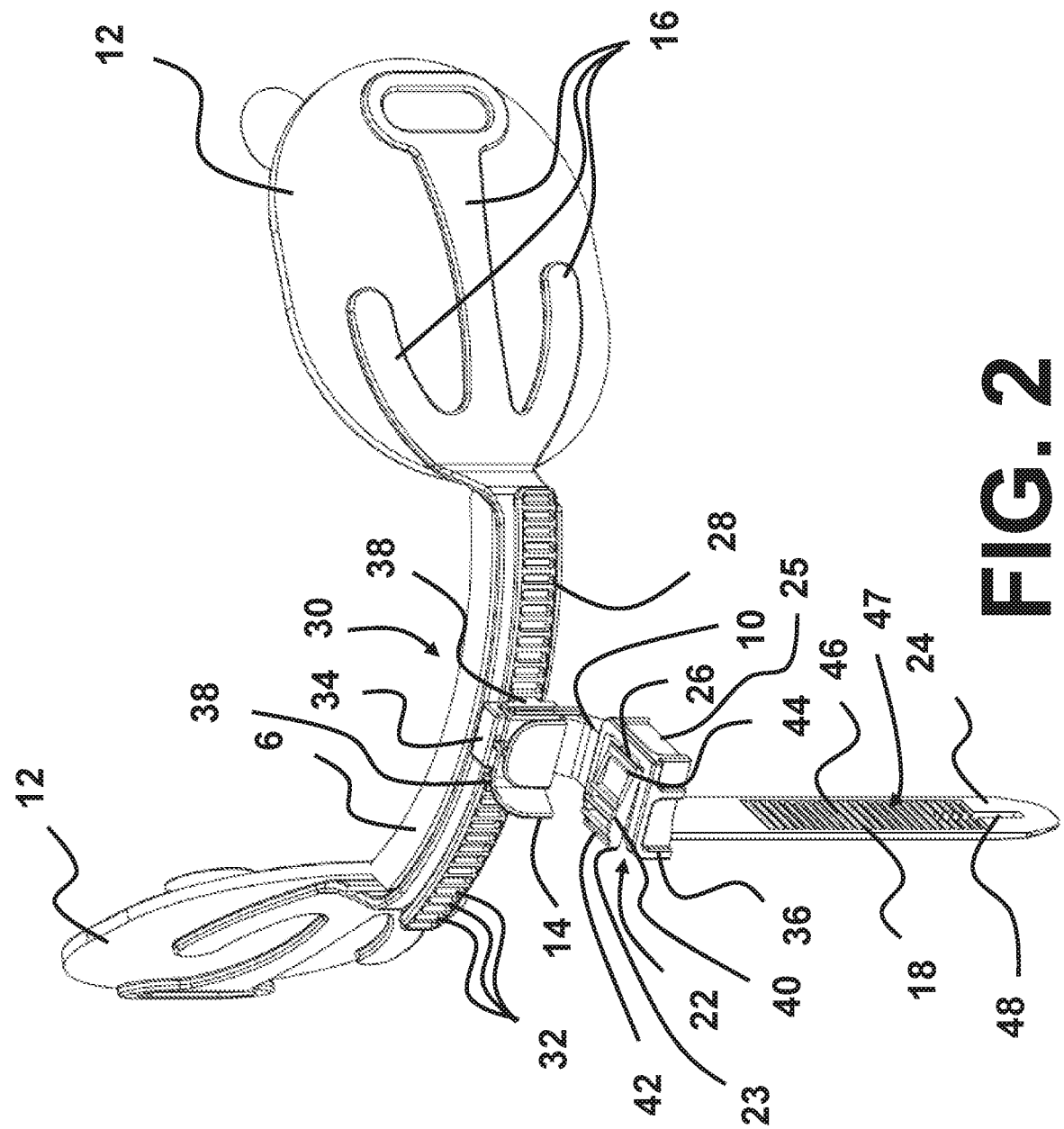
FIG. 2 is a perspective view of an endotracheal tube holder device.

As shown in FIGS. 1 and 2, the endotracheal tube 4 is secured to the tube holder base 20 via a tie 18. As shown in FIG. 1, a first end region 22 of the tie 18 is coupled to a first side 23 of tube holder base 20. The tie 18 is wrapped around the endotracheal tube 4 in a counterclockwise fashion with a second end region 24 of the tie 18 fitting through a slot 26 on a second side 25 of the tube holder base 20. The second end region 24 may also be fixed to the tube holder base 20 after it has passed through the slot 26. Because the tube holder base 20 is coupled to the lever arms 14, the endotracheal tube 4 may be repositioned laterally along the length of the rail 6.

As shown in FIG. 2, the tube holder is coupled to the rail 6 via the lever arms 14. The rail 6 has an exterior surface 28 and an interior surface 30, with the interior surface 30 making contact with the patient's face. There are a plurality of grooves 32 formed into the exterior surface 28 of the rail 6. The grooves 32 are configured to engage with the lever arms 14 of the tube holder 10. The grooves may have a variety of shapes, such as, for example, a discorectangular shape as shown in FIG. 2.

The tube holder 10 includes a positioning mechanism 34 and a tube holder base 20. The tube holder base 20 extends laterally away from the positioning mechanism 34 at a substantially perpendicular angle. The specific geometry between the tube holder base 20 and the positioning mechanism 34 may vary depending on the desired orientation of the tube holder 10. The lever arms 14 include prongs 38 that project towards the rail 6. The prongs 38 are positioned to engage the plurality of grooves 32 on the rail 6. When the lever arms 14 are disengaged, the prongs 38 rest within the grooves 32 to prevent lateral movement of the lever arms 14 and the tube holder 10 with respect to the rail 6.

The lever arms 14 may be engaged by compressing the lever arms 14 together. When the lever arms 14 are engaged, the prongs 38 will be actuated out of the grooves 32 and no longer restrict lateral movement of the lever arms 14 and the tube holder 10 with respect to the rail 6, such that the tube holder 10 can be repositioned relative to the rail 6. The repositioning may be desirable in situations where medical personnel may want to conduct a procedure around the patient's face or within the patient's mouth without having to remove the endotracheal tube 4.

The tube holder 10 includes a pawl 40 coupled to the tube holder base. The pawl can be, for example, a lever. The pawl 40 and the tube holder 10 define a slot 26 on a second side 25 of the tube holder base 20. The pawl 40 may be actuated to increase the size of the slot 26, allowing the tie 18 to pass through the slot 26. The pawl 40 may have a raised region 42 located at the first side 23 of the tube holder base 20 and a catch region 44 located at the second side 25 of the tube holder base 20. The thickness of the pawl 40 may taper from the raised region 42 towards the catch region 44. The pawl 40 may be actuated by applying a downward pressure onto the raised region 42 of the pawl 40, which will raise the catch region 44 and increase the size of the slot 26. The tube holder 10 also includes a tab 43 that extends laterally from the far side of the tube holder base (shown in FIGS. 5 and 6).

The first end region 22 of the tie 18 is fixed to the first side 23 of the tube holder base 20. The tie 18 may be fixed via an adhesive, a fastener, a frictional fit, a mechanical bond, or some other method known in the art. The tie 18 has a plurality of teeth 46 on a first surface 47 of the tie 18. The first surface 47 of the tie 18 contacts the endotracheal tube 4 when the tie 18 is wrapped around the endotracheal tube 4 to secure the endotracheal tube 4 to the tube holder base 20. The plurality of teeth 46 on the first surface 47 increases the friction between the tie 18 and the outer surface of an endotracheal tube 4 to help prevent lateral or rotational movement of the endotracheal tube 4. The tie 18 also includes a slit 48 at a second end region 24. As shown in FIG. 2, the slit 48 extends along a length of the tie 18; however, in other aspects, the slit 48 may extend along a width of the tie 18.

To secure an endotracheal tube 4 to the tube holder 10, the endotracheal tube 4 is placed below the tube holder base 20. The tie 18 is then wrapped around the endotracheal tube 4 and the second end region 24 of the tie 18 is inserted into the slot 26 on the tube holder base 20. The pawl 40 and the tie 18 act as a ratchet that will permit the tie 18 to be pulled upwards through the tube holder base 20, but restrict movement of the tie 18 in the opposite direction. In particular, the catch region 44 of the pawl 40 engages with the plurality of teeth 46 on the tie 18 and clamps down to prevent movement of the tie 18. To fully secure the endotracheal tube 4, the tie 18 should be pulled taut and the slit 48 on the tie 18 will be received around the tab 43 on the first side 23 of the tube holder base 20.

In order to release the endotracheal tube 4 from the tube holder 10, the slit 48 of the second end region 24 may be removed from the tab 43 on the tube holder base 20. The pawl 40 may then be actuated by applying a downward force on the raised region 42. This should cause the catch region 44 of the pawl 40 to unclamp and disengage from the teeth 46 of the tie 18, and the tie 18 may be pulled through the slot 26 to release the endotracheal tube 4.

Figure 3:
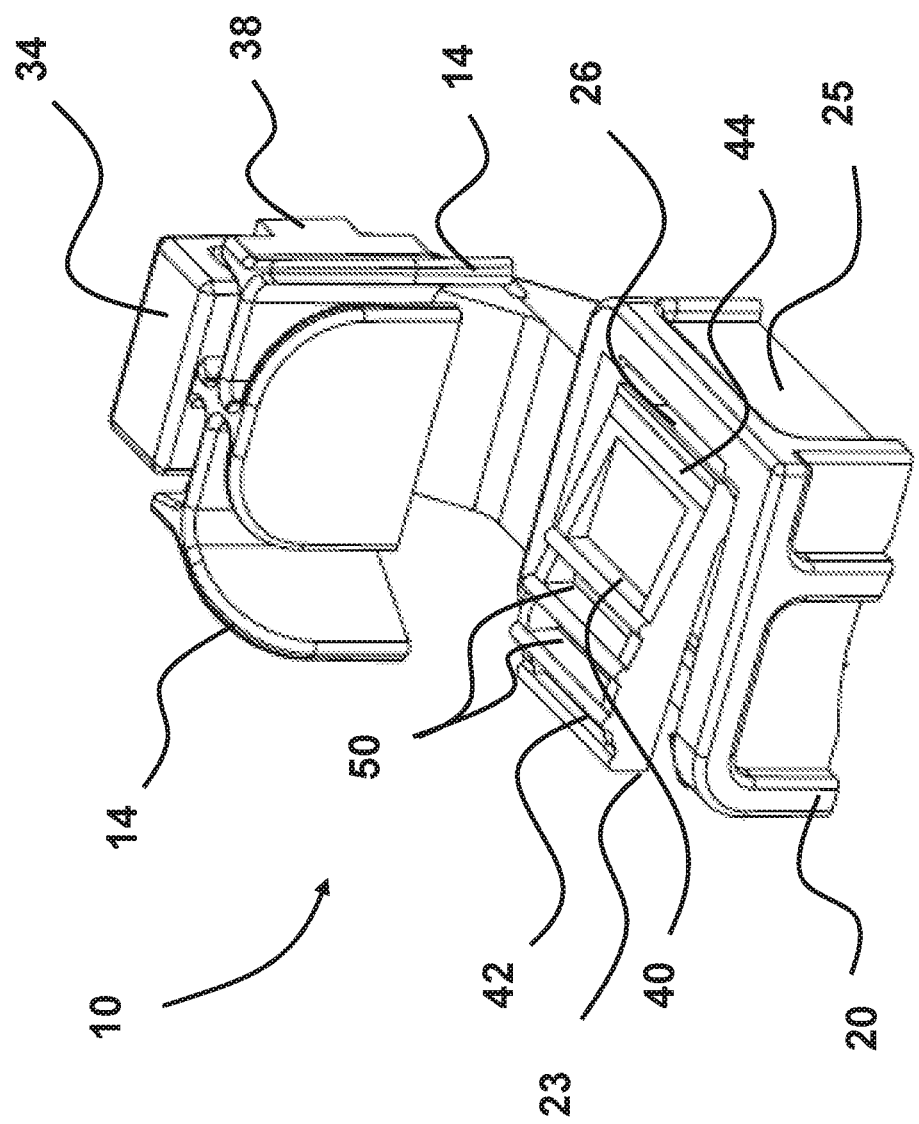
FIG. 3 is a perspective view of a tube holder of one aspect of the endotracheal tube holder device.

FIG. 3 illustrates the tube holder 10 portion of the endotracheal tube holder device 2. The prongs 38 of the lever arms 14 are configured to engage with the plurality grooves 32 on the rail 6. A plurality of indentations 50 on the raised region 42 of the pawl 40 provide tactile indication of the raised region 42 of the pawl 40. The tactile indication may allow the patient or practitioner to identify and actuate the raised region 42 of the pawl 40 without seeing the raised region 42.

Figure 4:
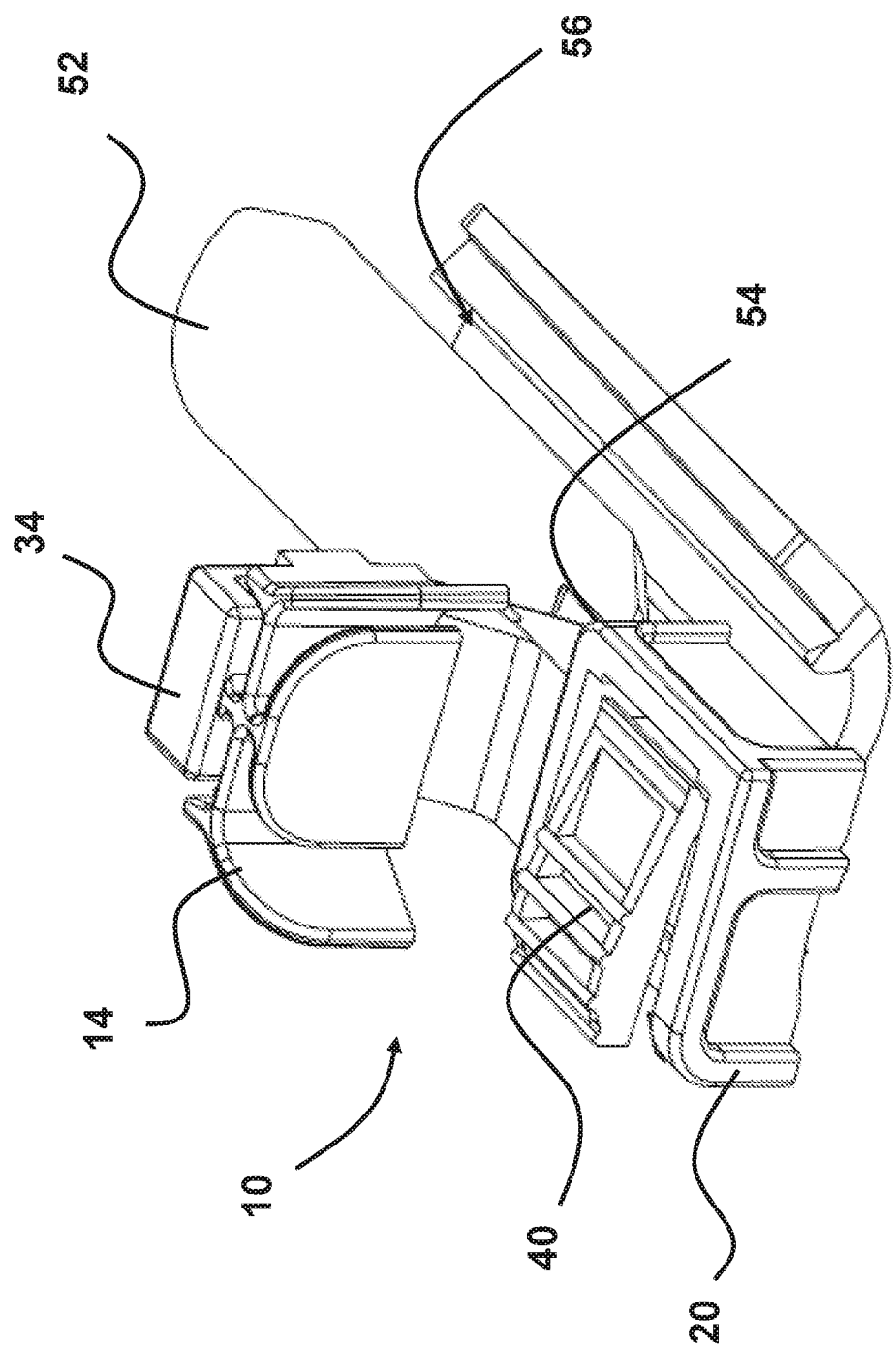
FIG. 4 is a perspective view of a tube holder with a bite block of another aspect of the endotracheal tube holder device.

FIG. 4 illustrates the tube holder 10 having a bite block 52 to prevent restriction of airflow through the endotracheal tube 4. During intubation, a patient may occasionally bite down on an endotracheal tube 4, which will restrict air flow through the endotracheal tube 4. A bite block 52 made from a more rigid material may be positioned around the endotracheal tube 4 and between the patient's teeth to protect the endotracheal tube 4. The bite block 52 may be made of the same material as the tube holder base 20.

The bite block 52 may be coupled to a rear end region 54 of the tube holder base 20. The bite block 52 extends from the tube holder base 20 towards the patient when the endotracheal tube holder device 2 is secured to the patient's face. The bite block 52 is comprised of a generally tubular wall having a substantially cylindrical shape. The bite block 52 may have an opening 56 extending along the length of the bite block 52 to allow an endotracheal tube 4 to be slid into the bite block 52.

As shown in FIG. 4, the bite block 52 can be integral with the tube holder 10, such that the tube holder 10 and the bite block 52 are a single piece. For example, the tube holder 10 comprising the tube holder base 20, the lever arms 14, the pawl 40, and the bite block 52 may be fabricated from the same material and may be formed through a single molding process. Alternatively, in some aspects, the bite block 52 may be a separate element from the tube holder 10, such that the bite block 52 may be secured to the tube holder 10 using an adhesive, mechanical fastener, or other securement methods known in the art.

Figure 5:
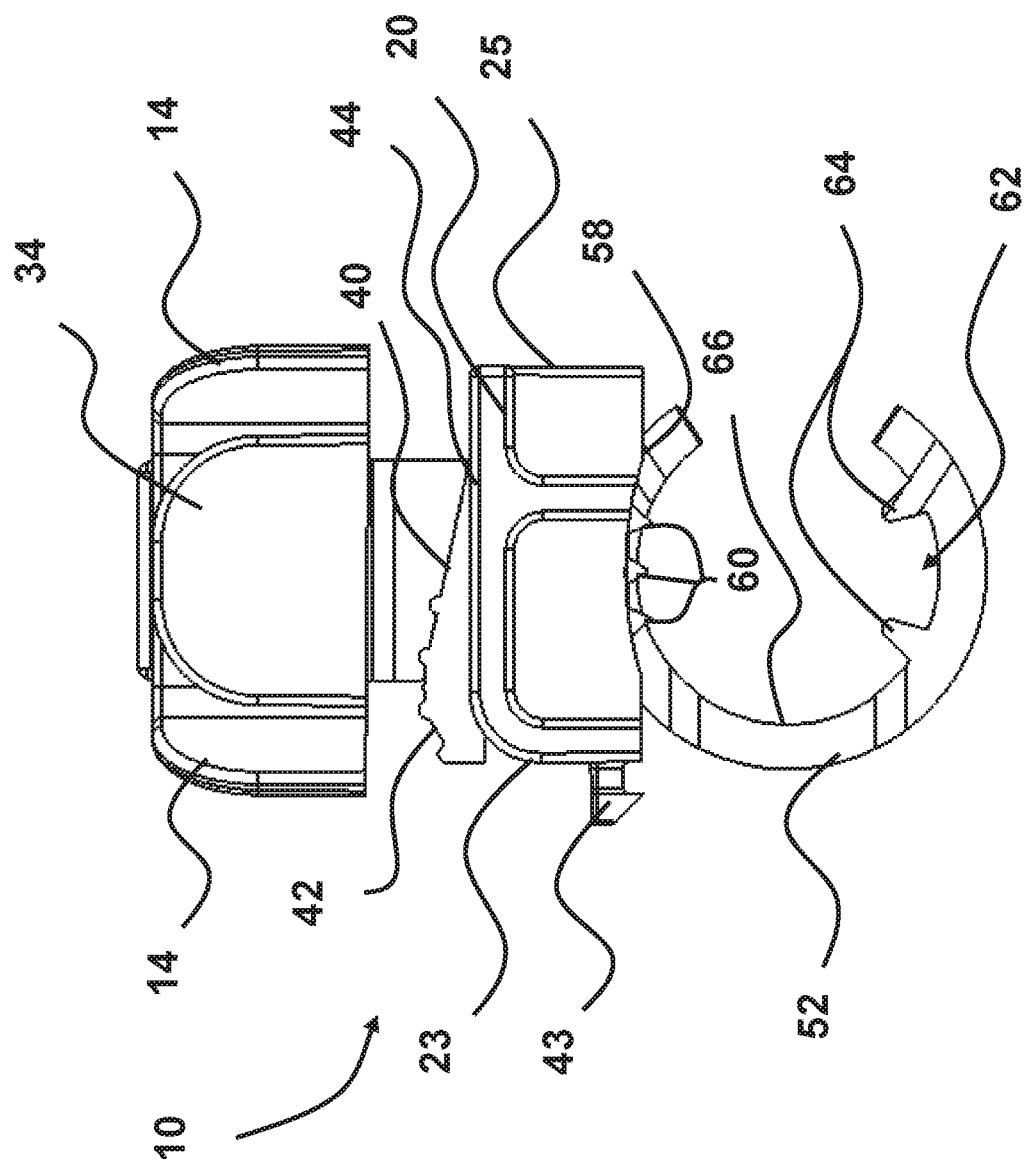
FIG. 5 is a front view of a tube holder with the bite block of the endotracheal tube holder device.

FIG. 5 illustrates a front view of the tube holder 10 and bite block 52. The raised region 42 of the pawl 40 is located towards the first side 23 of the tube holder base 20, while the catch region 44 of the pawl 40 is located towards the second side 25 of the tube holder base 20. Although hidden from view, the slot 26 defined between the pawl 40 and tube holder 10 is also located towards the second side 25 of the tube holder base 20. The bottom surface 58 of the tube holder base 20 also includes a plurality of barbs 60 to engage an endotracheal tube 4.

The bite block 52 is also coupled to the bottom surface 58 of the tube holder base 20. The bite block 52 may have a channel 62 defined between ribs 64 extending from an inner surface 66 of the bite block 52. The ribs 64 may extend along the length of the bite block 52 on the inner surface 66. Often additional passageways accompany the endotracheal tube 4, such as accessory lines or suctions lines. To prevent restriction of these additional passageways, these accessory lines may be placed into the channel 62.

FIG. 5 also illustrates the tab 43 described previously extending laterally from the first side 23 of the tube holder base 20. The tab 43 is configured to be received into the slit 48 of the tie 18. The tab 43 may have a knob shape in order to facilitate the insertion of the tab 43 through the slit 48. Once the slit 48 is received around the tab 43, the tab 43 may help prevent the tie 18 from loosening around an endotracheal tube 4.

Figure 6:
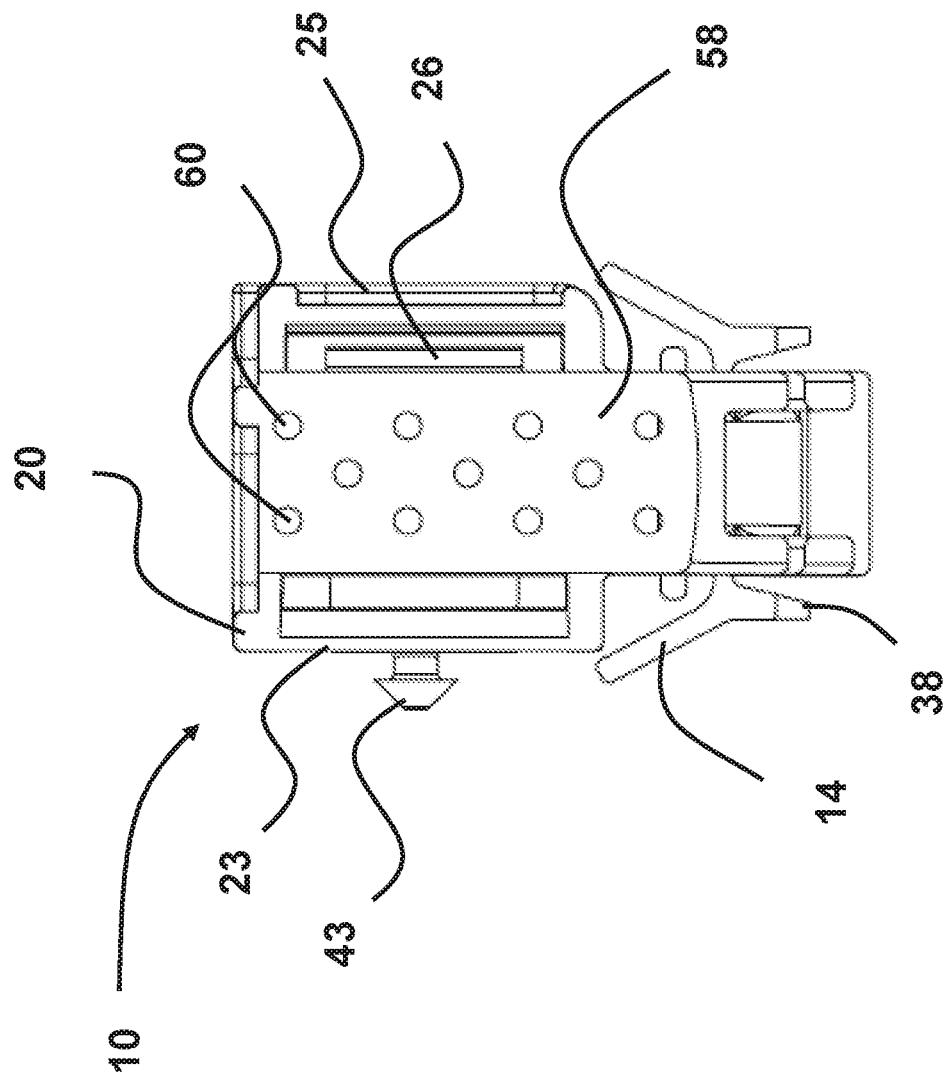
FIG. 6 is a bottom view of a tube holder of one aspect of the endotracheal tube holder device.

FIG. 6 illustrates a bottom view of the tube holder 10 without the bite block 52. The tube holder base 20 includes a tab 43 extending laterally from a first side 23 of the tube holder base 20 opposite from the second side 25 with the slot 26. As the tie 18 (not shown) is fit through the slot 26 of the tube holder base 20, the tie 18 will continue to wrap around the top of the tube holder base 20 and the tab 43 will be fit into slit 48 of the tie 18. The bottom surface 58 of the tube holder base 20 includes a plurality of barbs 60 to engage an endotracheal tube 4 and help prevent lateral or rotational movement of the endotracheal tube 4. The plurality of barbs 60 may be formed into the tube holder base 20 with a variety of patterns. The barbs 60 may be slightly rounded at their ends to prevent puncture of the endotracheal tube 4.

Figure 7:
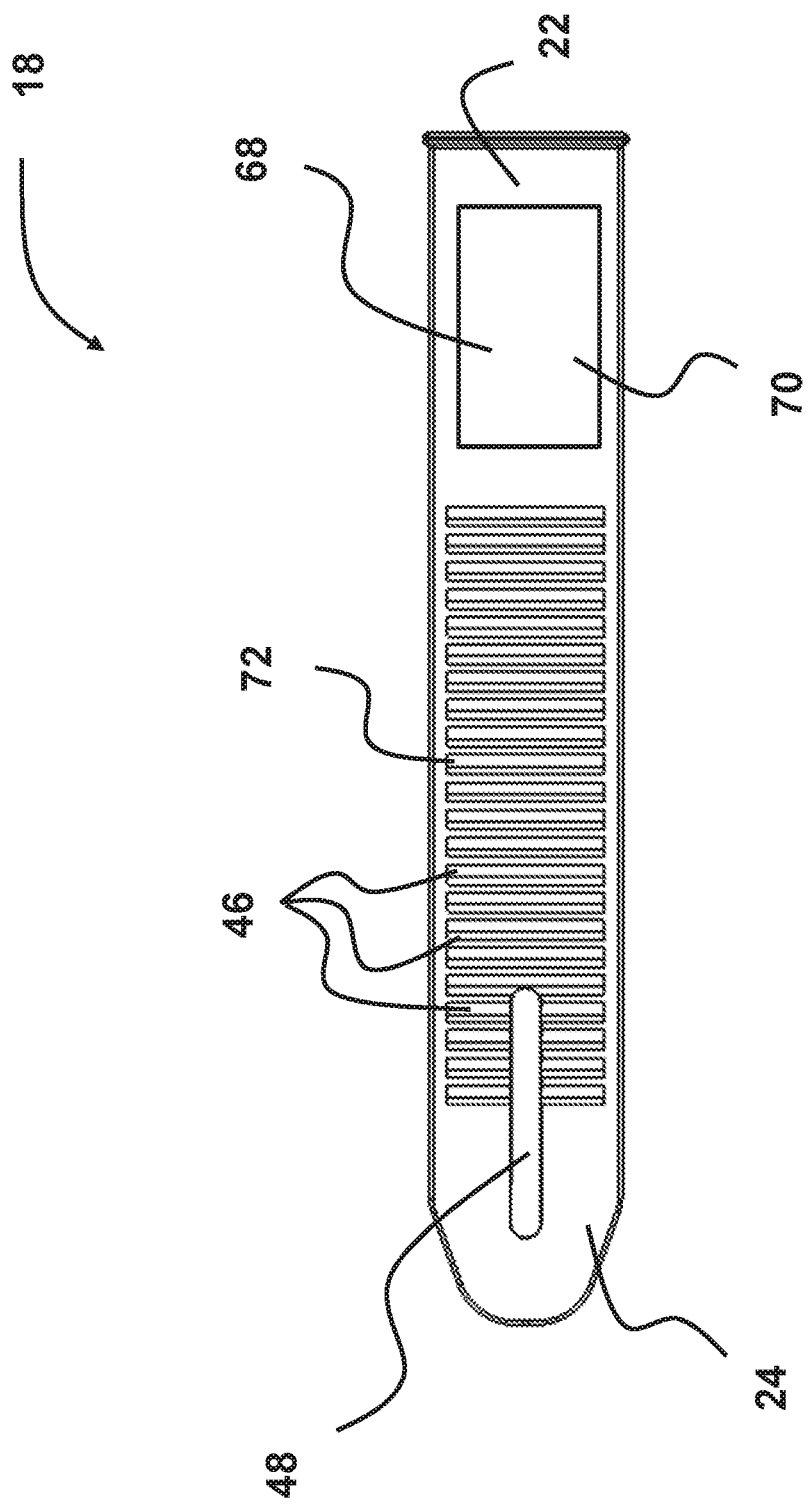
FIG. 7 is a top view of a tie of one aspect of the endotracheal tube holder device.

FIG. 7 illustrates a top view of a tie 18 according to one aspect. At a first end region 22 of the tie, an adhesive tape 68 may be applied to a first portion 70 of the tie 18. The adhesive tape 68 may provide additional securement of the endotracheal tube 4 to the tube holder base 20 and help prevent any lateral or rotational movement of an endotracheal tube 4. A plurality of teeth 46 are located in a middle strip 72 of the tie 18. The teeth 46 are engaged by the pawl 40 of the tube holder 10 to secure an endotracheal tube 4. In some aspects, each teeth 46 on the tie 18 extends linearly across the width of the tie 18. However, in other aspects, the teeth 46 can have a different pattern, such as a curve, on the tie 18. At the second end region 24 of the tie 18, the tie 18 may have a tapered shape to facilitate fit through the slot 26 on the tube holder base 20. As shown in FIG. 7, the tie 18 also has a slit 48 located in the second end region 24 of the tie 18 and may overlap with the plurality of teeth 46 in an overlapping region. In other aspects, the slit 48 may not overlap with the plurality of teeth 46.

FIG. 8 illustrates a top view of a tie 18 according to another aspect. The plurality of teeth 46 on the tie 18 may be implemented with different patterns across the width of the tie 18. A middle strip 72 of the plurality of teeth 46 may have a horizontal pattern across the width of the tie 18 while the two side strips 74 adjacent to the middle strip 72 may have a slanted pattern. The implementation of multiple patterns may increase the friction of the tie 18 against an endotracheal tube 4 and restrict both lateral and rotational movement of the endotracheal tube 4. Although the pattern on the side strips 74 is slanted towards the second end region 24 in FIG. 8, the pattern on the side strips 74 may also be slanted towards the first end region 22 of the tie 18. Alternatively, other patterns such as curves or waves may be implemented on the middle strip 72 or the side strips 74. Although FIG. 8 only depicts the patterns of the plurality of teeth 46 varying across the width of the tie 18, the patterns of the plurality of teeth 46 may also vary along the length of the tie 18 in addition to or instead of the variance along the width.

Figure 10:
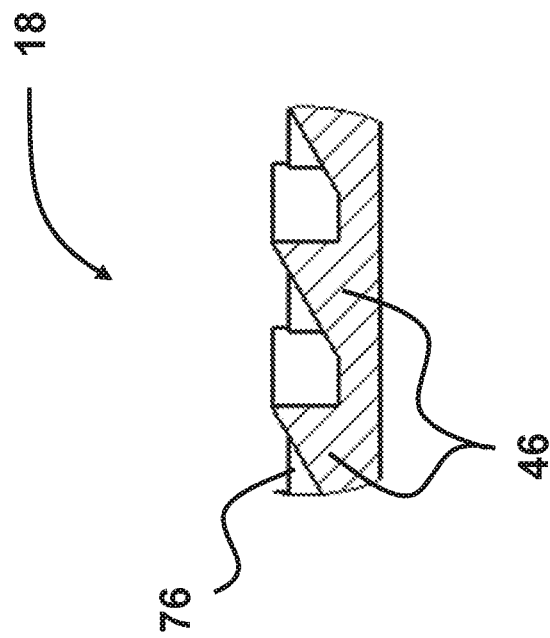
FIG. 10 is a partial side view of another version of the teeth of the ties shown in FIG. 9.
Figure 9:
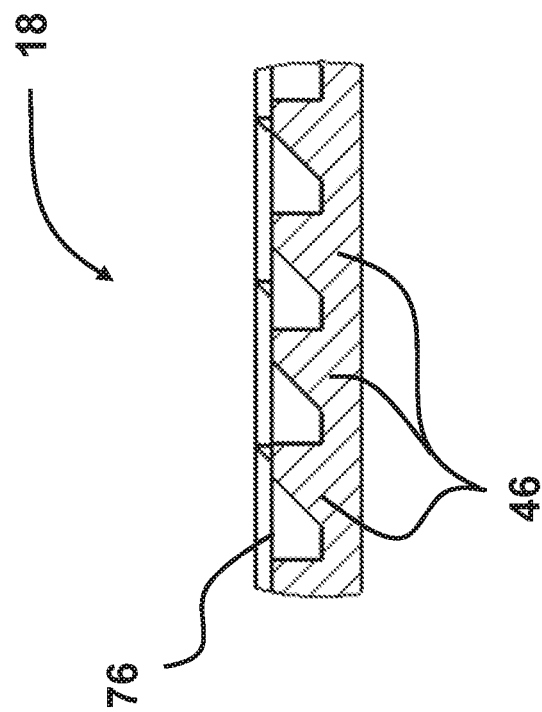
FIG. 9 is a partial side view of ties of another aspect of the endotracheal tube holder device.

FIGS. 9 and 10 illustrate side views of the plurality of teeth 46 of the tie 18. The plurality of teeth 46 may be formed on the tie 18 with different shapes including a sawtooth wave, a square wave, a rectangular wave, a trapezoidal wave, and a triangular wave. For example, FIG. 9 illustrates the teeth 46 implemented as trapezoidal waves, while FIG. 10 illustrates the teeth 46 implemented as sawtooth waves. In addition, the plurality of teeth 46 may be formed from a combination of the aforementioned shapes, such as alternating between a square wave shape and a triangular wave shape. The plurality of teeth 46 may also be formed within the surface 76 of the tie 18, as shown in FIG. 9, or the plurality of teeth may be formed to extend from the surface 76 of the tie 18, as shown in FIG. 10.

While the endotracheal tube holder device has been described in terms of what may be considered to be specific aspects, the disclosure need not be limited to the disclosed aspects. Additional modifications and improvements to the endotracheal tube holder device may be apparent to those skilled in the art. As such, this disclosure is intended to cover various modifications and similar arrangements included within the spirit and scope of the claims, the scope of which should be accorded the broadest interpretation so as to encompass all such modifications and similar structures. The present disclosure should be considered as illustrative and not restrictive.

The invention claimed is:

1. A device for holding an endotracheal tube, the device comprising:
   a rail having opposite ends and a plurality of grooves at least partially along the length of the rail between the opposite ends;
   a tube holder coupled to and slidable relative to the rail between the opposite ends, the tube holder including:
      at least one lever arm partially received within the grooves of the rail to allow lateral repositioning of the tube holder relative to the rail;
      a base extending in a direction relative to the at least one lever arm;
      a tie having an inner surface, a plurality of teeth on the inner surface, a first end region coupled to the base, and a second end region; and
      a pawl configured to engage at least one of the teeth of the tie and secure the tie around the endotracheal tube;
   wherein the second end region is configured to be pulled past the pawl and the base is configured to secure the second end region to a side of the base;
   wherein the plurality of teeth on the inner surface of the tie are disposed along a length of the tie and are configured to contact a portion of the endotracheal tube when the tie is secured around the endotracheal tube, such that the plurality of teeth on the inner surface of the tie are operable to increase friction between the tie and an outer surface of the endotracheal tube to secure endotracheal tube to the base;
   wherein the base and the pawl define a slot configured to receive the second end region of the tie; and
   wherein the pawl is operable to increase the size of the slot to allow the tie to pass through the slot.

2. The device of claim 1, further comprising an adhesive tape applied to a surface of the tie, wherein the surface of the tie is configured to contact a surface of the endotracheal tube.

3. The device of claim 2, wherein the adhesive tape is applied to the first end region of the tie.

4. The device of claim 1, wherein the tube holder includes a bite block configured to extend into a mouth of a patient.

5. The device of claim 4, wherein the bite block has a substantially cylindrical shape defining an axial opening along an entirety of a length of the bite block.

6. The device of claim 1, wherein the pawl defines a lever configured to be depressed and release the tie.

7. The device of claim 1, wherein a bottom surface of the base includes a plurality of barbs configured to engage the endotracheal tube.

8. The device of claim 1, further comprising a hydrocolloid pad coupled to each of the opposite ends of the rail.

9. The device of claim 1, wherein the at least one lever arm is configured to be laterally compressed to laterally reposition the tube holder relative to the rail.

10. The device of claim 1, wherein the plurality of teeth have a pattern selected from the group consisting of a sawtooth wave, a square wave, a rectangular wave, a trapezoidal wave, a triangular wave, and a combination thereof.

11. The device of claim 1, wherein the plurality of teeth comprise a first section along a width of the tie having a first pattern and a second section along the width of the tie outside of the first section having a second pattern, the second pattern being different from the first pattern.

12. The device of claim 1, wherein the rail is configured to be placed above a lip of a patient.

13. A kit, comprising:
   an endotracheal tube; and
   the device for holding the endotracheal tube of claim 1.

14. The device of claim 1, wherein the first end region of the tie is fixed to the first side of the base.

15. A device for holding an endotracheal tube, the device comprising:
   a rail having opposite ends and a plurality of grooves at least partially along the length of the rail between the opposite ends;
   a tube holder coupled to and slidable relative to the rail between the opposite ends, the tube holder including:
      at least one lever arm partially received within the grooves of the rail to allow lateral repositioning of the tube holder relative to the rail;
      a base extending in a direction relative to the at least one lever arm,
      a tie having a plurality of teeth, a first end region coupled to the base, and a second end region, and
      a pawl configured to engage at least one of the teeth of the tie and secure the tie around the endotracheal tube; and
   wherein the second end region is configured to be pulled past the pawl and the base is configured to secure the second end region to a side of the base,
   wherein the second end region of the tie defines a slit, and
   wherein a tab extends laterally from a portion of the base and is configured to be received within the slit defined by the tie.

16. The device of claim 15, wherein the tab includes a knob having a diameter greater than a width of the slit.

17. The device of claim 15, wherein the slit extends at least partially along an axial length of the tie.

18. The device of claim 15, wherein the slit extends at least partially across the plurality of teeth.

19. A device for holding an endotracheal tube, the device comprising:
   a rail having opposite ends and a plurality of grooves at least partially along the length of the rail between the opposite ends;
   a tube holder coupled to and slidable relative to the rail between the opposite ends, the tube holder including:
      at least one lever arm partially received within the grooves of the rail to allow lateral repositioning of the tube holder relative to the rail;
      a base extending in a direction relative to the at least one lever arm;

a tie having an inner surface, a plurality of teeth on the inner surface, a first end region coupled to the base, and a second end region; and a pawl configured to engage at least one of the teeth of the tie and secure the tie around the endotracheal tube;

wherein the second end region is configured to be pulled past the pawl and the base is configured to secure the second end region to a side of the base;

wherein the plurality of teeth on the inner surface of the tie are disposed along a length of the tie and are configured to contact a portion of the endotracheal tube when the tie is secured around the endotracheal tube, such that the plurality of teeth on the inner surface of the tie are operable to increase friction between the tie and an outer surface of the endotracheal tube to secure endotracheal tube to the base; and wherein the tie is configured to be wrapped around a top portion of the base.

20. The device of claim 19, wherein a bottom surface of the base includes a plurality of barbs configured to engage the endotracheal tube.

21. The device of claim 19, wherein the tube holder includes a bite block configured to extend into a mouth of a patient.

22. A device for holding an endotracheal tube, the device comprising:

a rail having opposite ends and a plurality of grooves at least partially along the length of the rail between the opposite ends;

a tube holder coupled to and slidable relative to the rail between the opposite ends, the tube holder including:
at least one lever arm partially received within the grooves of the rail to allow lateral repositioning of the tube holder relative to the rail;
a base extending in a direction relative to the at least one lever arm,
a tie having a plurality of teeth, a first end region coupled to the base, and a second end region, and
a pawl configured to engage at least one of the teeth of the tie and secure the tie around the endotracheal tube; and wherein the second end region is configured to be pulled past the pawl and the base is configured to secure the second end region to a side of the base, and wherein a tab extends laterally from a first portion of the base, the tab operable to retain the tie around the endotracheal tube and prevent the tie from loosening around the endotracheal tube.

23. The device of claim 22, wherein the plurality of teeth are formed on a surface of the tie, and wherein the surface of the tie is configured to contact a surface of the endotracheal tube.

* * * * *